(12) United States Patent
Beder et al.

(10) Patent No.: US 11,173,065 B2
(45) Date of Patent: Nov. 16, 2021

(54) EYE SURGERY METHOD AND EYE SURGERY SYSTEM

(71) Applicant: Carl Zeiss Meditec AG, Jena (DE)

(72) Inventors: Christian Beder, Aalen (DE); Frank Keib, Aalen (DE); Yorck von Bülow, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 79 days.

(21) Appl. No.: 16/432,300

(22) Filed: Jun. 5, 2019

(65) Prior Publication Data

US 2020/0383832 A1    Dec. 10, 2020

(51) Int. Cl.
*G06K 9/00* (2006.01)
*A61F 9/007* (2006.01)
*A61B 3/14* (2006.01)
*A61B 5/00* (2006.01)
*A61B 17/00* (2006.01)
*A61B 90/00* (2016.01)

(52) U.S. Cl.
CPC .......... *A61F 9/00736* (2013.01); *A61B 3/14* (2013.01); *A61B 5/7485* (2013.01); *A61B 2017/00061* (2013.01); *A61B 2090/373* (2016.02)

(58) Field of Classification Search
None
See application file for complete search history.

(56) References Cited

U.S. PATENT DOCUMENTS

2018/0140179 A1    5/2018  LaBelle et al.
2018/0147087 A1*   5/2018  Bacher ................. A61B 3/0008

* cited by examiner

*Primary Examiner* — Soo Jin Park
(74) *Attorney, Agent, or Firm* — Butzel Long

(57) ABSTRACT

The present invention relates to an eye surgery method and an eye surgery system. An eye surgery method comprises directing illumination light direction onto a target object of an eye; generating an observation image from observation light emerging from the target object due to scattering of the illumination light at the target object; highlighting, in the observation image, a region of interest characterized by a specific wavelength range by modifying the observation light or by modifying digital raw image data representing a spatial intensity distribution of the observation light; and identifying the target object in the observation image including the highlighted region of interest and manipulating at least one part of the identified target object.

13 Claims, 2 Drawing Sheets

EYE SURGERY METHOD AND EYE SURGERY SYSTEM

FIELD

The present invention relates to an eye surgery method and an eye surgery system configured to be applicable for executing the eye surgery method. In particular, the present invention relates to a vitrectomy surgery method, a cataract surgery method and eye surgeries relating to the cornea of an eye.

BACKGROUND

Eyes of humans or animals comprise multiple elements which are transparent for visible light such as the cornea, lens and vitreous humor. During eye surgeries these transparent elements (also referred to as target objects) are manipulated. For example, during a vitrectomy surgery, the vitreous humor is removed from the interior of the eye. During a cataract surgery, the lens is removed from the interior of the eye. During an eye surgery on the cornea, the cornea is manipulated by replacing or removing parts of the cornea.

Due to the fact that these target objects are transparent for visible light, it is generally difficult to observe these target objects during surgery and discriminate them from the surrounding parts of the eye.

A conventional method for observing target objects of an eye is to illuminate these target objects using visible light and to observe only scattered light. This means that neither direct illumination light nor reflected illumination light, but only scattered illumination light is used for observing the target objects. Rayleigh scattering of the illumination light at the target objects causes illumination light having short wavelengths to be scattered much stronger than illumination light having longer wavelengths. Using white light illumination, the short wavelength portion of the illumination light is scattered much stronger than the long wavelength portion of the illumination light. Consequently, the target objects of the eye observed by using only the scattered light appear in short wavelengths, e.g. blue, and, therefore, the target objects can be identified and discriminated from the surrounding parts of the eye.

This conventional method can be performed by selecting the illumination direction along which target objects are illuminated and the observation direction along which target objects are observed so that essentially only scattered light and neither direct illumination light nor reflected illumination light propagates along the observation direction. Therefore, the scattered light in the observation direction is not overpowered by direct illumination light and reflected illumination light which allows to identify the target objects in images generated from the scattered illumination light.

In order to make this conventional method work, relatively high intensities of light having short wavelengths must be used to illuminate the target objects. This can damage the eye. Therefore, it is desired to reduce the intensity of light having short wavelengths for illuminating the target objects. This however reduces the amount of scattered light and therefore makes it difficult to observe target objects of the eye using scattered light.

SUMMARY

An object of the present invention is to provide an eye surgery method and an eye surgery system allowing to observe and manipulate target objects of the eye while reducing the intensity of illumination light having short wavelengths in order to decrease damage to the eye caused by illumination light.

The above problem is solved by an eye surgery method comprising: directing illumination light onto a target object of an eye; generating an observation image from observation light emerging from the target object due to scattering of the illumination light at the target object; highlighting, in the observation image, a region of interest characterized by a specific wavelength range by modifying the observation light or by modifying digital raw image data representing a spatial intensity distribution of the observation light; and identifying the target object in the observation image including the highlighted region of interest and manipulating at least one part of the identified target object.

The target object can be located inside the eye.

The target object is illuminated and observed so that, at best, only scattered light is collected for generating the observation image, i.e., at best, direct illumination light and reflected illumination light do not contribute to the observation image. Accordingly, the target object is illuminated and observed so that essentially only scattered illumination light contributes to the observation light, i.e., so that the observation light is dominated by the illumination light scattered at the target object.

An example for achieving this specific illumination and observation situation is to direct the illumination light onto the target object along an illumination direction and to observe the target object from an observation direction, i.e., to observe the observation light emerging from the target object along the observation direction. The illumination direction is oblique to an optical axis of a lens of the eye, in particular an angle formed between the illumination direction and the optical axis of the lens of the eye can amount to a value of at least 10° or at least 20° and at most 90°. Further, the observation direction can be oblique to the illumination direction, in particular an angle formed between the observation direction and the illumination direction can amount to a value of at least 10° or at least 20° and at most 90. With this configuration, essentially only scattered light contributes to the observation light.

Other techniques to make the observation light comprise essentially only scattered illumination light can be applied. For example, in order to reduce the amount of reflected illumination light contributing to the observation light, a light absorber can be introduced into the eye, for example between the retina and the vitreous humor (as the target object). The light absorber is configured to absorb the illumination light, in particular to absorb the illumination light having transmitted the vitreous humor (target object). Accordingly, illumination light which would otherwise be reflected at the retina is absorbed by the light absorber, thereby reducing the amount of reflected illumination light contributing to the observation light.

According to another example, the amount of reflected illumination light contributing to the observation light is reduced by selecting the illumination direction and the observation direction to not be oriented perpendicular to reflective material interfaces of the eye.

In contrast to the above-described conventional method, the observation image generated from the observation light comprises a highlighted region of interest representing the target object. Due to the highlighting of the region of interest, the target object can be identified more easily. The region of interest is a portion of the observation image and is characterized by its spectral properties, e.g. the region of interest is generated from scattered light having essentially only wavelengths of the specific wavelength range.

For example, the highlighting of the region of interest can be performed by modifying the observation light itself. For example, the observation light can be filtered by an optical filter suppressing the observation light having wavelengths outside the specific wavelength range. This enhances the perception of the region of interest and eliminates the necessity for an increased intensity of the illumination light.

In addition or alternatively, the highlighting of the region of interest can be performed by modifying digital raw image data representing a spatial intensity distribution of the observation light. For example, a digital raw image representing the spatial intensity distribution of the observation light can be recorded and the recorded digital raw image, represented by the digital raw image data, can be modified in order to highlight the region of interest in the raw image, thereby generating the observation image. Also this enhances the perception of the region of interest and eliminates the necessity for an increased intensity of the illumination light.

The above-described eye surgery method can be a vitrectomy surgery method and, therefore, the target object can be vitreous humor. In this case, the illumination light is scattered at the vitreous humor and the observation image is generated from the illumination light scattered at the vitreous humor. The vitreous humor can be identified in the observation image due to the characteristic color of scattered light of the specific wavelength range. At last, the vitreous humor can be removed from the interior of the eye using a vitrectomy surgery tool, for example.

The above-described eye surgery method can be a cataract surgery method and, therefore, the target object can be the lens of the eye. In this case, the illumination light is scattered at the lens and the observation image is generated from the illumination light scattered at the lens. The lens can be identified in the observation image due to the characteristic color of scattered light of the specific wavelength range. At last, the lens can be removed from the interior of the eye using a cataract surgery tool (e.g., an emulsification tool), for example.

Further, the target object can be the cornea of the eye. In this case, the illumination light is scattered at the cornea and the observation image is generated from the illumination light scattered at the cornea. The cornea can be identified in the observation image due to the characteristic color of scattered light of the specific wavelength range. At last, the cornea can be manipulated using a surgery tool.

The specific wavelength range characterizing the region of interest can be a wavelength range of visible light. In particular, a maximum wavelength of the specific wavelength range can be 700 nm or 600 nm. A minimum wavelength of the specific wavelength range can be 400 rm. A bandwidth of the specific wavelength range can be at least 50 nm. Accordingly, the region of interest is characterized by scattered light of the blue and green spectral range.

The illumination light can be white light, i.e., comprise light having wavelengths in a range of 400 nm to 760 nm. In particular, the illumination light comprises light having wavelengths of the specific wavelength range. In particular, the illumination light can further comprise light having wavelengths outside the specific wavelength range.

An eye surgery method according to the present invention can comprise any of the above described tasks performed by any of the components of the above-described eye surgery systems. Further, any of the above-described eye surgery systems is configured to be applicable for executing the surgical methods described herein.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
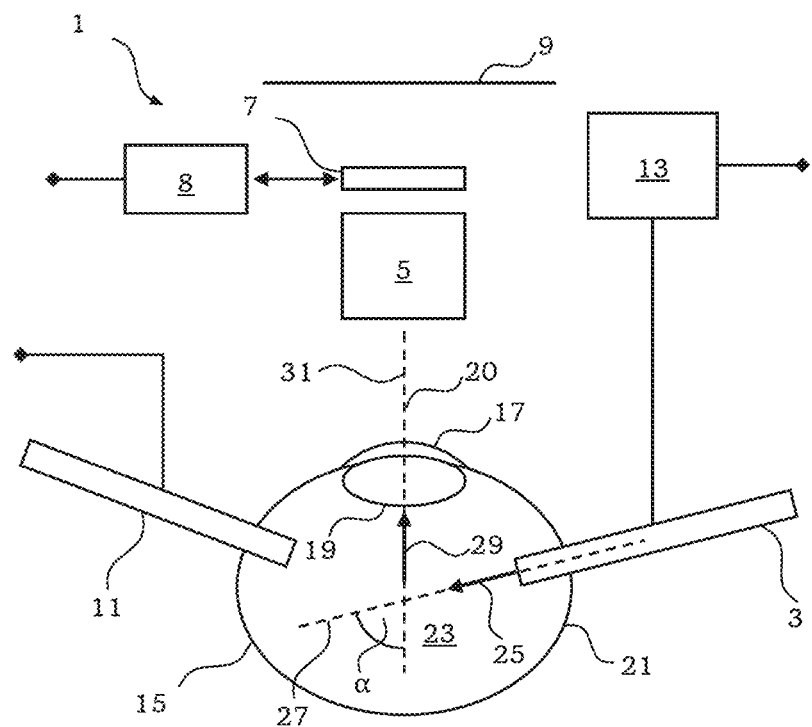
FIG. 1 shows a schematic illustration of an eye surgery system according to a first embodiment of the present invention.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

FIG. 1 shows a schematic illustration of an eye surgery system 1 according to a first embodiment of the present invention. The eye surgery system 1 comprises an illumination light source 3, observation optics 5, an observation filter 7, an actuator 8, an eye surgery tool 11 and a controller 13.

FIG. 1 further shows a schematic illustration of an eye 15. The eye 15 comprises a cornea 17, a lens 19 having an optical axis 20, a retina 21 and vitreous humor 23 in the interior of the eye 15. The optical axis 20 is a principle axis of the lens 19 of the eye 15.

The illumination light source 3 is configured to generate illumination light 25 and to direct the illumination light 25 along an illumination direction 27. As illustrated in FIG. 1, the illumination light source 3 can be partly introduced into the eye 15 for directing the illumination light 25 onto a target object inside the eye 15. Depending on the particular application of the eye surgery system 1, the target object can be the cornea 17, the lens 19 or the vitreous humor 23, for example. In the example illustrated in FIGS. 1 and 2, the target object is the vitreous humor 23.

The observation optics 5 provide an imaging system for visible light. The observation optics 5 are configured to generate an image of the target object in the image plane 9. An observer can observe the image generated by the observation optics 5 in the image plane 9. For example, an ocular can be used for observing said image or an image detector can be used to detect the image generated in the image plane 9.

The observation optics 5 can be configured to generate an observation image from observation light 29 emerging from the target object along an observation direction 31. The observation light 29 results from scattering of the illumination light 25 at the target object. As illustrated in FIG. 1, the observation light 29 is collected by the observation optics 5 to generate the observation image in the image plane 9. Also, as illustrated in FIG. 1, the observation direction 31 and the optical axis 20 of the lens 19 of the eye 15 can be parallel to each other or coincide.

Figure 2:
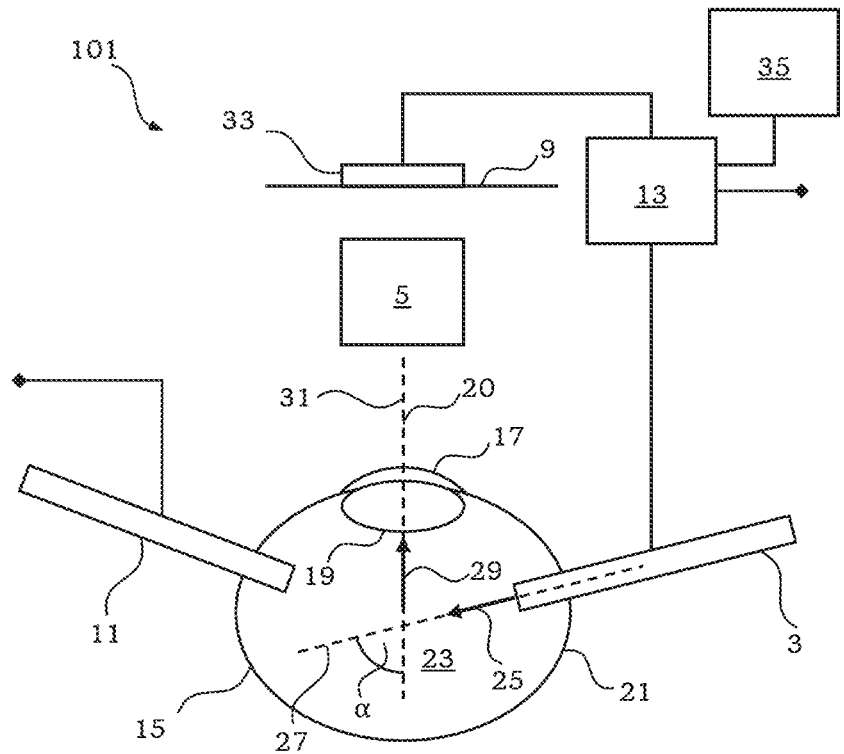
FIG. 2 shows a schematic illustration of an eye surgery system according to a second embodiment of the present invention.

As illustrated in FIGS. 1 and 2, the illumination direction 27 is oblique to the optical axis 20 of the lens 19 of the eye 15. An angle α formed between the illumination direction 27 and the optical axis 20 of the lens 19 of the eye 15 can amount to a value of at least 10° or at least 20° and at most 90°. Further, the observation direction 31 can be oblique to the illumination direction 27. In particular an angle formed between the observation direction 31 and the illumination direction 27 can amount to a value of at least 10° or at least 20° and at most 90°. Because e observation direction 31 and the optical axis 20 of the lens 19 of the eye 15 coincide in the example illustrated in FIG. 1, the angle formed between the observation direction 31 and the illumination direction 27 corresponds to the angle α formed between the illumination direction 27 and the optical axis 20 in this case. This, however, is a special case and in general, both angles can be different.

The observation filter 7 can be disposed in a beam path of the observation optics 5 in order to modify the observation light 29. The observation filter 7 is configured to transmit observation light 29 having wavelengths within the specific wavelength range at a high transmission while suppressing observation light 29 having wavelengths outside the specific wavelength range. Thereby, observation light 29 having wavelengths within the specific wavelength range contributes stronger to the observation image compared to the observation light 29 having wavelengths outside the specific wavelength range. Therefore, a region of interest characterized by the specific wavelength range is highlighted in the observation image.

The actuator 8 is configured to move the observation filter 7 into the beam path provided by the observation optics 5 and out of said beam path. This is illustrated by a double arrow in FIG. 1. The actuator 8 is controlled by the controller 13.

Using the observation image including the highlighted region of interest, the target object can be identified in the observation image by a surgeon, for example. Further, at least one part of the identified target object can be manipulated, removed or replaced by a surgeon, for example. The eye surgery tool 11 can be used for manipulating the target object. The eye surgery tool 11 can be a vitrectomy tool, a cataract tool and the like, for example.

The controller 13 is connected to the illumination light source 3 for controlling the illumination light source 3. The controller 13 is also connected to the actuator 8 for controlling the actuator 8. The controller 13 is also connected to the eye surgery tool 11 for controlling the eye surgery tool 11. The connection between the controller 13 and the actuator 8 and the eye surgery tool 11, respectively, is illustrated by a connection line which, only for the sake of clarity of the Figures, is interrupted by diamonds.

With this configuration, the illumination light 25 scattered at the target object is used for generating an observation image of the target object. In addition, the observation filter 7 highlights a region of interest characterized by the specific wavelength range in the observation image.

According to a specific mode of operation of the eye surgery system 1, the controller 13 controls the actuator 8 to move the observation filter 7 into the beam path provided by the observation optics 5 and controls the illumination light source 3 to emit illumination light 25 when the eye surgery tool 11 is used or prepared for use. According to another mode of operation of the eye surgery system 1, the controller 13 controls the actuator 8 to move the observation filter 7 out of the beam path provided by the observation optics 5 when the eye surgery tool 11 is not used.

FIG. 2 shows a schematic illustration of an eye surgery system 101 according to a second embodiment of the present invention. The eye surgery system 101 is similar to the eye surgery system 1 illustrated in FIG. 1.

The eye surgery system 101 comprises the illumination light source 3, the observation optics 5, the eye surgery tool 11 and the controller 13. The eye surgery system 101 can further comprise the observation filter 7. The eye surgery system 101 further comprises an image detector 33 and a display 35.

The image detector 33 is disposed in the image plane 9 in order to capture an image formed in the image plane 9 by the observation optics 5. The image detector 33 can be a color camera, for example. The controller 13 is connected to the image detector 33 for obtaining the image captured by the image detector 33.

The display 35 is configured to display an image provided by the controller 13.

In particular, the image detector 33 can be configured to detect a digital raw image of the target object using observation light 29 imaged into the image plane 9 by the observation optics 5. Therefore, the digital raw image represents a spatial intensity distribution of the observation light in the image plane 9. The digital raw image can be represented by digital raw image data. The controller 13 can be configured to analyze and process the digital raw image. In particular, the controller 13 can highlight the region of interest in the digital raw image to thereby generate the observation image to be displayed on the display 35.

For example, the image detector 33 can be a color camera providing multiple different color channels for detecting a spatial intensity distribution for each of multiple different at most partially overlapping wavelength ranges. I.e., multiple spatial intensity distributions are detected from observation light of different wavelength ranges. The color camera can be a RGB-color camera providing color channels for red, green and blue wavelength ranges, for example. Accordingly, a spatial intensity distribution of observation light having wavelengths in the blue wavelength range, a spatial intensity distribution of observation light having wavelengths in the green wavelength range and a spatial intensity distribution of observation light having wavelengths in the red wavelength range can be detected and used separately for generating the observation image.

The highlighting of the region of interest can comprise generating the observation image based on at least one but not all of the detected spatial intensity distributions. For example, only the color channel for the blue wavelength range is used for generating the observation image, thereby using only strongly scattered illumination light. Alternatively, only the color channel for the green wavelength range can be used for generating the observation image, thereby also using essentially only scattered illumination light. In general, among the color channels provided by a color camera, only the color channel including the shortest wavelengths or the adjacent color channel having longer wavelengths can be used for generating the observation image. I.e., other color channels are not used for generating the observation image.

Alternatively, the highlighting of the region of interest comprises generating the observation image based on weighted spatial intensity distributions, wherein the weighted spatial intensity distributions are obtained by weighting the detected spatial intensity distributions by at least partially different factors. Because the factors used for weighting the detected spatial intensity distributions are at least partially different, the contribution of some of the detected spatial intensity distributions to the observation image is enhanced over the contribution of the other spatial intensity distributions. Thereby, the region of interest is highlighted, wherein the specific wavelength range corresponds wavelength ranges of the color channels used for detecting the spatial intensity distributions weighted high.

For example, the RGB-color camera providing color channels for red, green and blue wavelength ranges is used. The "blue" spatial intensity distribution is weighted by a factor of 2 while the "green" and "red" spatial intensity distributions are weighted by a factor of 1. The specific wavelength range corresponds to the wavelength range of the color channel for the blue wavelength range. Accordingly, "blue" observation light contributes stronger to the observation image than "green" and "red" observation light. Thereby, the region of interest is highlighted.

Other color cameras providing multiple different color channels different from red, green and blue can be used as well.

According to another example, the controller 13 can be configured to identify the region of interest in the detected raw image based on a spectral analysis of the detected raw image. In this example, some or all of the color channels provided by a color camera can be used for identifying the region of interest.

For example, the region of interest can be identified in the detected raw image as a region in which a spectral intensity for at least one wavelength within the specific wavelength range is greater than a threshold value. In this case, pixels of the detected raw image are identified as the region of interest, said each of the pixels having a spectral intensity for at least one wavelength within the specific wavelength range which is greater than the threshold value. The threshold value can be a predetermined constant or be determined based on the detected raw image. For example, the threshold value is determined from the detected raw image based on at least one spectral intensity for at least one wavelength outside the specific wavelength range.

Several different approaches for identifying the region of interest in the detected raw image were presented above. However, the person skilled in the art appreciates that many other possibilities for identifying the region of interest based on the detected raw image exist and can be applied as required.

As described above, in the second embodiment, the controller 13 is configured to highlight the region of interest in order to generate the observation image. Several different possibilities of highlighting the region of interest are described with reference to FIG. 3.

Figure 3:
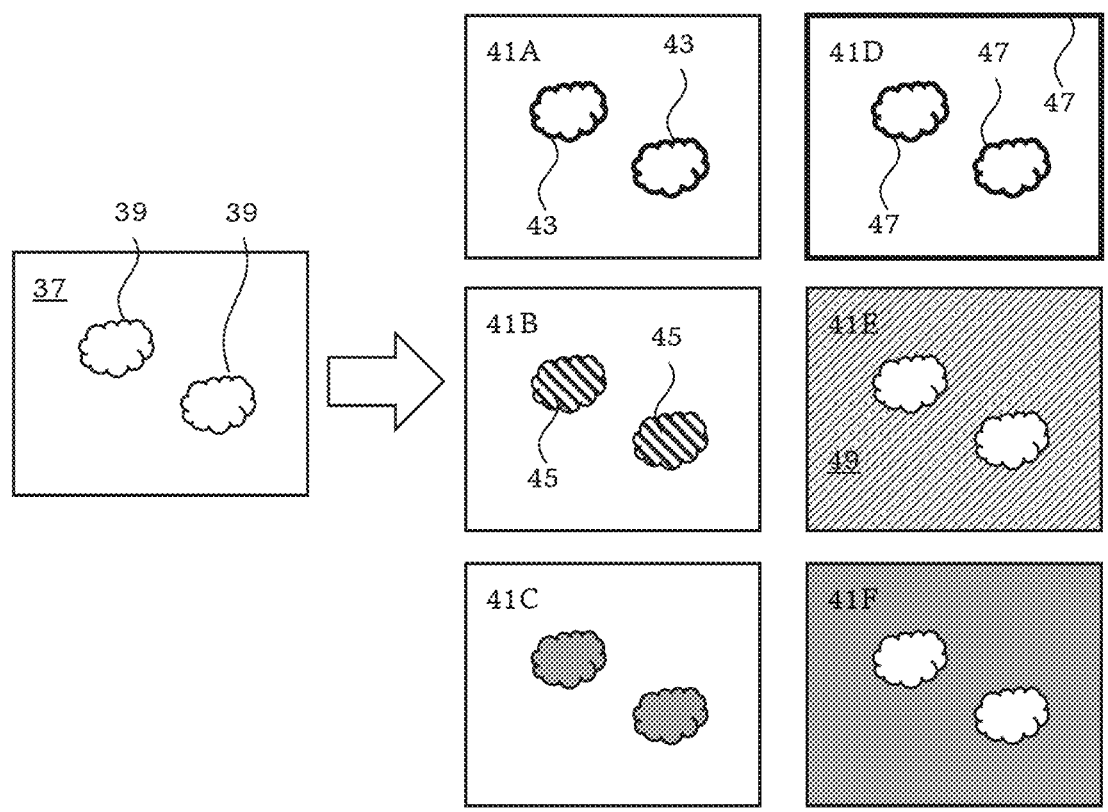
FIG. 3 shows examples of observation images comprising highlighted regions of interest.

FIG. 3 shows a raw image 37 containing two separate regions of interest 39. The regions of interest 39 are not highlighted in the raw image 37. However, as described above, the controller 13 can be configured to identify the regions of interest 39 in the detected raw image 37 based on a spectral analysis of the detected raw image 37.

For example, the controller 13 can be configured to generate an observation image 41A by highlighting a boundary 43 of the regions of interest 39. For example, the controller 13 introduces a boundary line into the raw image 37 in order to generate the observation image 41A.

For example, the controller 13 can be configured to generate an observation image 41B by highlighting an area 45 of the regions of interest 39. The area 45 is highlighted by hatching, for example.

The controller 13 can be configured to generate an observation image 41C by changing at least one of brightness, hue and saturation of the regions of interest 39. In the example of the observation image 41C illustrated in FIG. 3, the regions of interest 39 are highlighted by changing the hue of the regions of interest 39.

For example, the controller 13 can be configured to generate an observation image 41D by highlighting a boundary of a region of the observation image 41D outside the regions of interest 39, thereby implicitly highlighting the regions of interest 39.

For example, the controller 13 can be configured to generate an observation image 41E by highlighting an area 49 of a region of the observation image 41E outside the regions of interest 39, thereby implicitly highlighting the regions of interest 39. In the example of the observation image 41E illustrated in FIG. 3, the area of the region of the observation image 41E outside the regions of interest 39 is highlighted by hatching.

For example, the controller 13 can be configured to generate an observation image 41F by changing at least one of brightness, hue and saturation of a region of the observation image 41F outside the regions of interest 39. In the example of the observation image 41C illustrated in FIG. 3, the region of the observation image 41F outside the regions of interest 39 is highlighted by changing the hue of said region.

The above-described examples for highlighting the regions of interest 39 can be combined and other mechanisms can be applied.

As illustrated in FIGS. 1 and 2, the observation light 29 can transmit through the lens 19 of the eye 15 before being collected by the observation optics 5 for generating the observation image.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

LIST OF REFERENCE NUMERALS 1, 101 eye surgery system; 3 illumination light source; 5 observation optics; 7 observation filter; 8 actuator; 9 image plane; 11 eye surgery tool; 13 controller; 15 eye; 17 cornea, 19 lens, 21 retina, 23 vitreous humor, 25 illumination light, 27 illumination direction; 29 observation light; 31 observation direction; 33 image detector; 35 display; 37 raw image; 39 region of interest; 41A to 41F observation image; 43 boundary of region of interest; 45 area of region of interest; 47 region of observation image outside the region of interest.

The invention claimed is:

1. An eye surgery method, comprising:
directing illumination light onto a target object of an eye;
generating an observation image from observation light emerging from the target object due to scattering of the illumination light at the target object;
highlighting, in the observation image, a region of interest characterized by a specific wavelength range by modifying digital raw image data representing a spatial intensity distribution of the observation light;
identifying the target object in the observation image including the highlighted region of interest and manipulating at least one part of the identified target object;

detecting a digital raw image of the target object using the observation light, wherein the digital raw image data represents the digital raw image; and displaying the observation image;

wherein the highlighting of the region of interest is based on the digital raw image;

wherein the detecting of the digital raw image comprises detecting a spatial intensity distribution for each of multiple different at most partially overlapping wavelength ranges of the observation light using a color camera providing multiple different color channels; and wherein the highlighting of the region of interest comprises generating the observation image based on at least one but not all of the detected spatial intensity distributions.

2. The eye surgery method according to claim 1, wherein the highlighting of the region of interest comprises at least one of:

highlighting a boundary of the region of interest, highlighting an area of the region of interest, changing at least one of brightness, hue and saturation of the region of interest, highlighting a boundary of a region of the observation image outside the region of interest, highlighting an area of a region of the observation image outside the region of interest, changing at least one of brightness, hue and saturation of a region of the observation image outside the region of interest.

3. The eye surgery method according to claim 1, wherein at least one of the following holds:

a maximum wavelength of the specific wavelength range is 700 nm, a minimum wavelength of the specific wavelength range is 400 nm, a bandwidth of the specific wavelength range is at least 50 nm.

4. The eye surgery method according to claim 1, wherein the illumination light is directed onto the target object along an illumination direction and the observation light emerges from the target object along an observation direction; and wherein at least one of the following holds:

the illumination direction is oblique to an optical axis of a lens of the eye;

an angle formed between the illumination direction and an optical axis of a lens of the eye amounts to a value of at least 20° and at most 90°;

the observation direction is oblique to the illumination direction;

an angle formed between the observation direction and the illumination direction amounts to a value of at least 20° and at most 90°.

5. The eye surgery method according to claim 1, wherein at least one of the following holds:

the illumination light is white light;

the illumination light comprises light having wavelengths of the specific wavelength range;

the observation light is transmitted through a lens of the eye.

6. The eye surgery method according to claim 1, wherein at least one of the following holds:

wherein the surgical method is a vitrectomy surgery method and the target object is vitreous humor;

the surgical method is a cataract surgery method, in particular an eye lens emulsification method, and the target object is a lens of the eye;

the target object is a cornea of the eye.

7. An eye surgery system configured to be applicable for executing the surgical method according to claim 1.

8. An eye surgery method, comprising:

directing illumination light onto a target object of an eye;

generating an observation image from observation light emerging from the target object due to scattering of the illumination light at the target object;

highlighting, in the observation image, a region of interest characterized by a specific wavelength range by modifying digital raw image data representing a spatial intensity distribution of the observation light;

identifying the target object in the observation image including the highlighted region of interest and manipulating at least one part of the identified target object;

detecting a digital raw image of the target object using the observation light, wherein the digital raw image data represents the digital raw image; and displaying the observation image;

wherein the highlighting of the region of interest is based on the digital raw image;

wherein the detecting of the digital raw image comprises detecting a spatial intensity distribution for each of multiple different at most partially overlapping wavelength ranges of the observation light using a color camera providing multiple different color channels; and wherein the highlighting of the region of interest comprises generating the observation image based on weighted spatial intensity distributions, wherein the weighted spatial intensity distributions are obtained by weighting the detected spatial intensity distributions by at least partially different factors.

9. An eye surgery method, comprising:

directing illumination light onto a target object of an eye;

generating an observation image from observation light emerging from the target object due to scattering of the illumination light at the target object;

highlighting, in the observation image, a region of interest characterized by a specific wavelength range by modifying digital raw image data representing a spatial intensity distribution of the observation light;

identifying the target object in the observation image including the highlighted region of interest and manipulating at least one part of the identified target object;

detecting a digital raw image of the target object using the observation light, wherein the digital raw image data represents the digital raw image;

displaying the observation image; and identifying the region of interest in the detected raw image based on a spectral analysis of the detected raw image;

wherein the highlighting of the region of interest is based on the digital raw image.

10. The eye surgery method according to claim 9, wherein the region of interest is identified in the detected raw image as a region in which a spectral intensity for at least one wavelength within the specific wavelength range is greater than a threshold value.

11. The eye surgery method according to claim 10, further comprising:

determining the threshold value from the detected raw image based on at least one spectral intensity for at least one wavelength outside the specific wavelength range.

12. An eye surgery method comprising:

directing illumination light onto a target object of an eye;

generating an observation image from observation light emerging from the target object due to scattering of the illumination light at the target object;

highlighting, in the observation image, a region of interest characterized by a specific wavelength range by modifying digital raw image data representing a spatial intensity distribution of the observation light; and identifying the target object in the observation image including the highlighted region of interest and manipulating at least one part of the identified target object;

wherein the target object is illuminated and observed so that the observation light is dominated by the illumination light scattered at the target object.

13. The eye surgery method according to claim 12, further comprising:

detecting a digital raw image of the target object using the observation light, wherein the digital raw image data represents the digital raw image; and displaying the observation image;

wherein the highlighting of the region of interest is based on the digital raw image.

\* \* \* \* \*